(12) United States Patent
Aiazian

(10) Patent No.: US 7,024,024 B1
(45) Date of Patent: Apr. 4, 2006

(54) SYSTEM FOR CONTRAST ECHO ANALYSIS

(75) Inventor: Aram Aiazian, Rotterdam (NL)

(73) Assignee: Axle International, The Hague (NL)

( * ) Notice: Subject to any disclaimer, the term of this patent is extended or adjusted under 35 U.S.C. 154(b) by 656 days.

(21) Appl. No.: 09/992,242

(22) Filed: Nov. 14, 2001

Related U.S. Application Data

(60) Provisional application No. 60/248,473, filed on Nov. 14, 2000.

(51) Int. Cl.
*G06K 9/00* (2006.01)

(52) U.S. Cl. .......................... 382/128; 382/130

(58) Field of Classification Search ................ 382/128, 382/130, 154; 128/916
See application file for complete search history.

(56) References Cited

U.S. PATENT DOCUMENTS

| | | | |
|---|---|---|---|
| 5,474,073 A | 12/1995 | Schwartz et al. | |
| 5,734,739 A * | 3/1998 | Sheehan et al. | 382/128 |
| 5,852,646 A * | 12/1998 | Klotz et al. | 378/8 |
| 5,883,613 A | 3/1999 | Iwaki | |
| 5,970,182 A | 10/1999 | Goris | |
| 5,993,391 A * | 11/1999 | Kamiyama | 600/443 |
| RE36,564 E | 2/2000 | Schwartz et al. | |
| 6,047,218 A | 4/2000 | Whayne et al. | |
| 6,171,246 B1 | 1/2001 | Guracar et al. | |
| 6,174,285 B1 * | 1/2001 | Clark | 600/443 |
| 6,186,949 B1 | 2/2001 | Hatfield et al. | |
| 6,221,015 B1 | 4/2001 | Yock | |
| 6,231,834 B1 | 5/2001 | Unger et al. | |
| 6,251,074 B1 | 6/2001 | Averkiou et al. | |
| 6,258,033 B1 | 7/2001 | Grenon | |
| 6,301,496 B1 * | 10/2001 | Reisfeld | 600/407 |

* cited by examiner

*Primary Examiner*—Jingge Wu
*Assistant Examiner*—Ashutosh Upreti
(74) *Attorney, Agent, or Firm*—Haugen Law Firm PLLP

(57) ABSTRACT

A system for imaging and analyzing perfusion in selected body regions includes an imaging device configured to transmit electronic signals to computer-executable software, the software being programmed to translate the electrical signals into electronic data, and to transpose and calculate such data into multi-dimensional displays, which multi-dimensional displays depict perfusion characteristics reflecting image data free of non-essential background data.

15 Claims, 2 Drawing Sheets

SYSTEM FOR CONTRAST ECHO ANALYSIS

CROSS-REFERENCE TO RELATED APPLICATION

This application claims priority from U.S. Provisional Application Ser. No. 60/248,473, filed Nov. 14, 2000, entitled "IMAGE ANALYSIS SYSTEM".

FIELD OF THE INVENTION

The present invention relates to medical imaging in general, and more particularly to image analysis of contrast echocardiograms. The present invention also contemplates the application of image analysis with a variety of medical imaging modalities, including angiography, CT scanning, magnetic resonance imaging, and other medical imaging applications.

BACKGROUND OF THE INVENTION

A variety of systems have been implemented to generate medical images of certain regions of the body. A particular application in which such medical imaging has proven to be instrumental in diagnosing and treating maladies is ultrasonic imaging of perfusion characteristics utilizing injected ultrasonic echocontrast material. Such echocontrast material allows ultrasonic image system operators to obtain perfusion characteristics important in diagnosing opacification and other blood flow problems. In particular applications, such ultrasonic imaging is utilized in imaging at least a portion of the myocardial perfusion, particularly the perfusion in the left ventricle.

Ultrasonic imaging systems proposed and implemented to date, however, have typically been used to assess the myocardial perfusion only in a single cross-section of a portion of the myocardium. In addition, conventional systems used for ultrasonic imaging have limited automated and semi-automated features for analyzing and displaying data and images pertinent to the relevant medical diagnosis. For example, present systems fail to automatically generate selected ultrasonic images, as well as automatically generating desired multi-dimensional segments of the region of interest. Such deficiencies generally hinder medical analysis of perfusion characteristics throughout the region of interest, including the entire targeted organ.

It is therefore a principle object of the present invention to provide an in vivo imaging system which automatically generates and displays multi-dimensional data and images of a region of interest.

It is a further object of the present invention to provide a system for obtaining and analyzing multi-dimensional in vivo images which is configured to automatically eliminate temporary or background data from targeted data prior to development of visually-perceivable data sets and images.

It is another object of the present invention to provide a system for obtaining and analyzing multi-dimensional in vivo images by collecting ultrasonic contrast data developed by transmitting ultrasonic energy into a region of interest having echocontrast material passing therethrough, which ultrasonic data is obtained over predefined time periods.

SUMMARY OF THE INVENTION

By means of the present invention, analysis of in vivo images, particularly those developed by ultrasonic imaging techniques, is enhanced by providing automated calculation and display of normalized data sets and multi-dimensional images. Analysis of such images is further enhanced by the system of the present invention by providing automated or semi-automated division of such in vivo images into user-defined multi-dimensional segments. Comparison studies of particular regions of interest are facilitated by simultaneously displaying corresponding regions of interest imaged at distinct periods of time. As with other aspects of the invention, such comparison images may be automatically normalized at the system operator's discretion. The system of the present invention is particularly adapted to calculate data relationships from electronic signals generated in ultrasonic contrast studies which utilize injected echocontrast material for analyzing perfusion characteristics.

One embodiment of the system of the present invention provides a method for obtaining and analyzing multi-dimensional in vivo images, which method includes providing computer-executable software operably configured to receive electronic signals via electronic communication means, wherein the software is programmed to translate the electronic signals into electronic data, and to calculate and format the electronic data into visually perceivable displays. The software is preferably programmed to automatically eliminate baseline data from the electronic data prior to development of such visually-perceivable displays. The method further includes providing an imaging device for generating the electronic signals representing corresponding image characteristics, wherein the imaging device is operably coupled to the communication means for operably transmitting the electronic image signals therethrough. To enable gathering of data, an echocontrast material is preferably injected into a targeted body region, with the body region being scanned by the imaging device in one or more predefined time periods. The method further includes displaying electronic images of the body region on a viewable screen, which electronic images represent a multi-dimensional view of the targeted body region, with the multi-dimensional view being automatically divided into user-defined segments for detailed analysis thereof.

A number of additional features may be incorporated into the system of the present invention. The software is preferably programmed to calculate individual pixel intensity change over respective time periods, and may also be programmed to calculate an overall intensity change for each respective segment. The software may also be programmed to display a plurality of selected multi-dimensional views obtained at distinct predetermined time periods, which time periods may include before and after medical treatment. The software may also calculate and display a relative data set reflecting changes in multi-dimensional view characteristics between such distinct predetermined time periods. In preferred embodiments, the software is programmed to automatically determine size and location of a perfusion defect area, and to automatically compare data from respective corresponding perfusion defect areas. The software is preferably programmed to selectively simultaneously display a plurality of time-intensity curves from one or more user-defined segments imaged in one or more respective time periods.

An additional embodiment of the present invention includes a system for imaging and analyzing perfusion in selected body regions, which system includes an ultrasonic intra-vascular imaging device operably coupled to electronic communication means, wherein the intra-vascular imaging device is operably positioned adjacent to respective body regions via a catheter means. The imaging device is preferably configured to operably transmit and receive ultrasonic energy, with the received ultrasonic energy being transformed into electronic signal indicative of ultrasonic contrast intensity measure. The system further includes a computer having computer-executable software stored thereon, wherein the computer is operably coupled to the electronic communication means for receiving electronic signals therefrom. The software is preferably programmed to translate the electrical signals into electronic data, and to transpose and calculate such data into multi-dimensional displays which are visually perceivable on a monitor operably coupled to the computer. The multi-dimensional displays preferably depict perfusion characteristics of the selected body region. Further, the software preferably automatically eliminates background data from the electronic data prior to calculating time-based ultrasonic echo intensity change.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
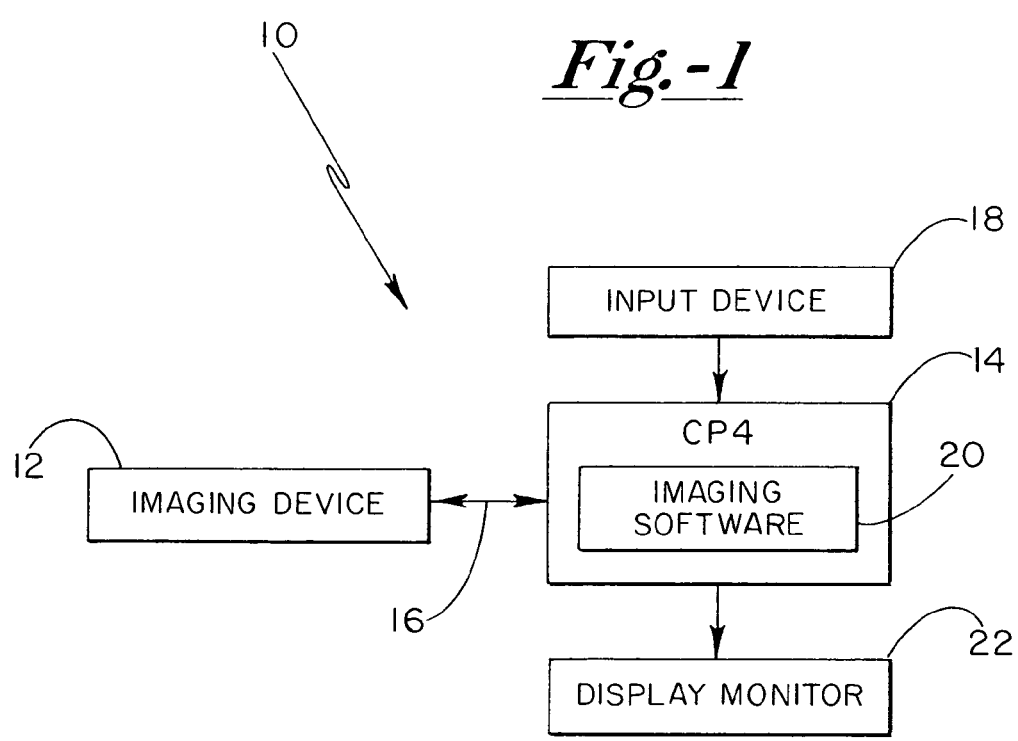
FIG. 1 is a schematic diagram illustrating the system of the present invention.

Referring now by characters of reference to the drawings, and first to FIG. 1, an in vivo imaging system 10 is shown. Imaging system 10 generally includes an in vivo imaging device 12 which is operably coupled to a computer or central processing unit (CPU) 14 via electronic communication means 16. Imaging device 12 is preferably coupled to a catheter means or other intra-vascular apparatus for positioning imaging device 12 adjacent a designated region of interest within the body. Imaging device 12 is therefore preferably positioned adjacent a targeted region of interest by passing into and through the body vasculature.

Electronic communication means 16 is preferably configured to operably connect imaging device 10 to CPU 14 throughout the imaging process. In some embodiments, electronic communication means 16 may include a wire or other physical electronic transmission means, but may also include remote wireless transmission means for emitting particular frequencies perceivable by CPU 14.

Imaging system 10 further includes an operator input device 18 operably coupled to CPU 14 for entering relevant instructions and data for imaging purposes. Input device 18 may include a keyboard, a remote pointer device, or other means for inputting information to CPU 14.

CPU 14 preferably includes imaging software 20 stored thereon for controlling and instructing imaging device 12, as well as for calculating and composing data obtained from imaging device 12 into relevant data sets and visually-perceivable image data. Such data sets and image data are preferably automatically delivered to display monitor 22 for review and analysis by the system operator. Display monitor 22 may include a computer monitor directly coupled to CPU 14, or any other viewable screen.

In preferred embodiments, imaging device 12 comprises an ultrasonic transducer that is operably controlled by imaging software 20 on CPU 14. Imaging device 12, however, may instead comprise any modality of imaging devices, including resonance imaging devices, CT scanning devices, angiography devices, and other medical imaging devices which may be configured to operate either in vivo or ex vivo. In operation, imaging device 12 transmits a signal into a predefined region of interest in the body. Preferably, a portion of the transmitted signal is reflected or returned to a receiver coupled to imaging device 12. The receiver is preferably configured to generate electronic signals from the returned transmission, and to subsequently transmit such electronic signals to CPU 14 through communication means 16. In a particular embodiment of the present invention, imaging device 12 includes an ultrasonic transducer which transmits ultrasonic energy to a region of interest in the body. In some embodiments, echocontrast material is injected into the region of interest either prior to, or during, the scanning procedure enabled by transmitting ultrasonic energy. The echocontrast material preferably reflects ultrasonic energy with relatively high efficiency such that locations within the region of interest having echocontrast material therein is perceived by imaging device 12 as a strongly reflected ultrasonic signal. In such a manner, perfusion characteristic studies may be performed via ultrasonic imaging techniques.

Imaging software 20 is preferably programmed to translate the electronic signals delivered thereto by imaging device 12 into relevant electronic data, and to calculate and format the electronic data into discrete data sets visually perceivable on display monitor 22. In preferred embodiments, imaging software 20 directs imaging device 12 to scan the region of interest for one or more predefined time periods, whereby image data may be sorted into discrete time period data sets by imaging software 20. In addition to scanning for, and obtaining data representing perfusion of echocontrast material, imaging device 12 is preferably directed to scan the region of interest to develop a baseline data set representing background noise and structures in the region of interest which are irrelevant to perfusion studies. Such background imaging provides imaging software 20 with data on ultrasonically reflective structures such as connective tissue, myocytes, and other background noise developed in the ultrasonic screening process. A plurality of such background screenings may be performed to develop an average, mean, median, or other background data set which imaging software 20 preferably uses to normalize perfusion study images.

Imaging software 20 is preferably programmed to automatically eliminate baseline data from electronic data generated during ultrasonic imaging of the region of interest. The elimination of baseline data is accomplished by subtracting a desired baseline data set from the acquired perfusion data sets prior to development of final data sets and displays delivered to display monitor 22 for analysis thereof. In such a manner, the system operator perceives images and data sets normalized so as to reflect only the data and images pertinent to the corresponding imaging procedures being performed. In preferred embodiments, such a normalization procedure is applicable to data sets obtained over predefined time periods of image scanning. In such a manner, normalized time-based data sets such as time-intensity curves displaying ultrasonic reflectivity in the region of interest over time may be presented to the system operator in a desired manner.

Once the desired image has been acquired, the system may be directed to analyze the acquired image through one or more techniques. In preferred embodiments, the user may choose particular regions of interest among multiple regions being defined in size and location by the user. In some embodiments of the present invention, six regions of any size and location may be defined and subsequently selected by the user to direct the system to analyze such regions. Data generated from distinct regions of interest may be simultaneously viewed and analyzed by the user. Such regional selection enables the user to study the temporary relationship between respective perfusion patterns of different regions simultaneously. The open designation and subsequent selection of user-defined regions is particularly useful for the analysis of the opacification of the cardiac chambers following contrast injection, and for abdominal and other ultrasound contrast studies.

Figure 2:
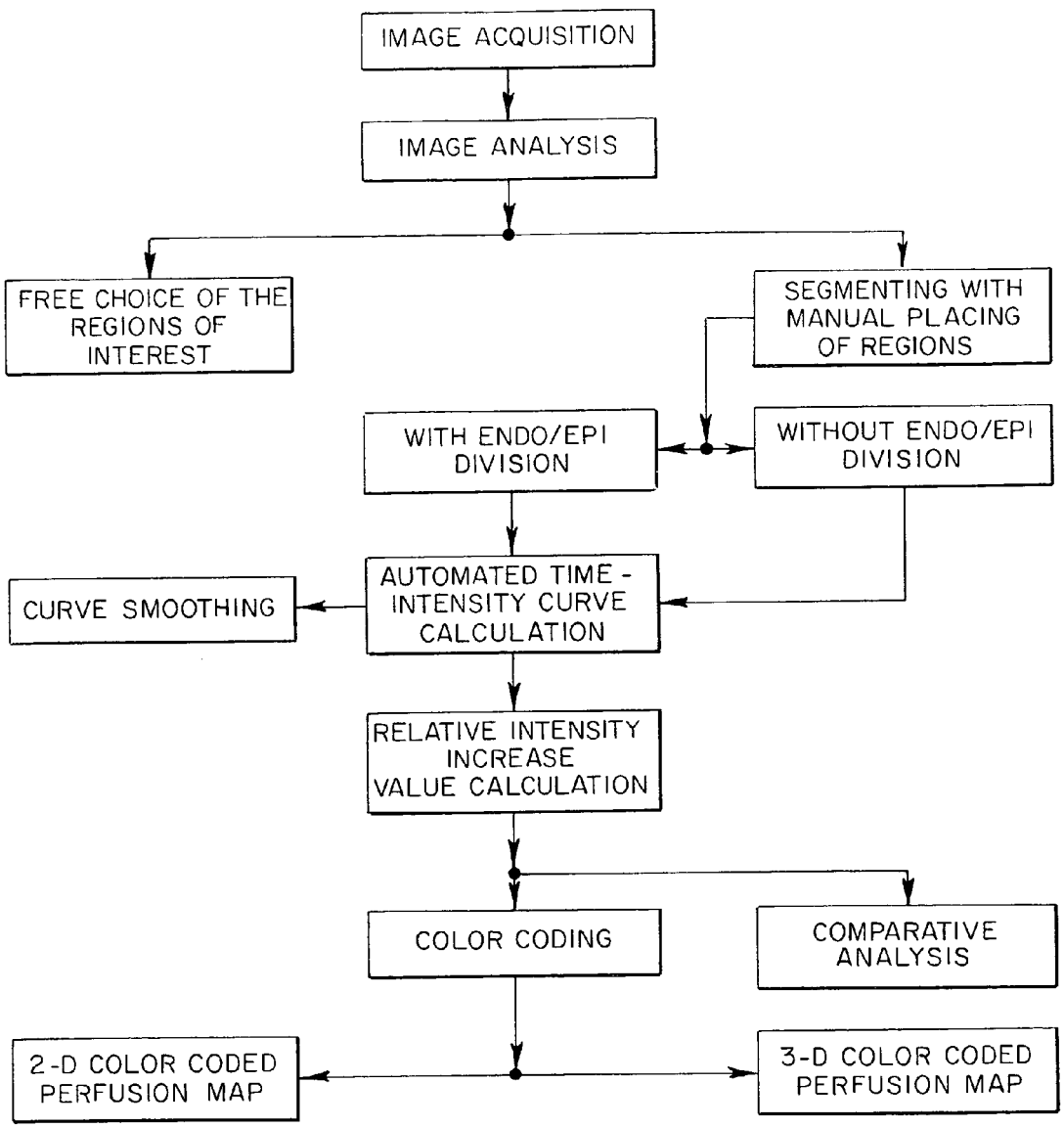
FIG. 2 is a flow diagram depicting an image acquisition, analysis, and display sequence in accordance with the system of the present invention.

The user may also choose to analyze the retrieved image through segmenting. Such a segmenting feature allows the user to divide the entire myocardium into distinct segments for sequential or simultaneous analysis. In preferred embodiments of the present invention up to 100 such segments may be designated in each view. As shown in the flowchart of FIG. 2, such segmenting may also be performed with, or without subendocardial/subepicardial (endo/epi) division. The endo/epi division feature enables the user to study subendocardial perfusion deficit data. The endo/epi division feature automatically calculates a time-intensity curve and its parameters in each designated segment.

Once the divisions or regions have been determined or designated by the user, the system preferably automatically calculates time-intensity curve data. Time-intensity curve parameters include maximal intensity increase, time of contrast appearance, time of maximal contrast increase, washout half time, rate of intensity increase, rate of intensity decrease, area under the curve, area under the curve until the washout half time, and area under the curve between the maximal contrast increase. The results of the analysis may then be displayed as individual curves and corresponding tables for each designated segment (region), and then simultaneously analyzed as side-by-side images on display monitor 22.

In preferred embodiments of the present invention, the imaging system further includes curve smoothing functionality for gradual smoothing of the original time-intensity curve data through various mathematical functions. Through such a curve-smoothing tool, results obtained and viewed by the user best reflect data trends, and reduce the impact of data aberrations on image analysis.

The system of the present invention preferably utilizes such time-intensity curves to generate relative intensity increase values for each designated segment (region). Such relative intensity increase values may be normalized and corrected as defined by the user through uniform or non-uniform normalization of all data of all segments utilized to generate a distinct data set. Such normalization is carried out by the system, which utilizes internal reference point, external reference point, arbitrary value, mean of all values, and baseline to normalize such data.

For easy comparison between the different segments of the same view, the system of the present invention automatically performs color coding of the retrieved image according to parameters set by the user. In preferred embodiments, a color bar with associated reference numbers is displayed together with the color-coded image to more distinctly identify particular data sets. This color-coded data may be generated as either a two-dimensional color-coded perfusion map, or a three-dimensional color-coded perfusion map. A three-dimensional representation preferably displays all of the selected region of interest segments, which are color-coded according to user definition. In preferred embodiments, anterior and posterior views of the particular region of interest is displayed simultaneously with the three-dimensional, rotating color-coded perfusion map of the left ventricle. The color coding may preferably be alternatively switched on or off at the direction of the user.

Preferably, the system is programmed to display multi-dimensional views of selected segments, or the entire region of interest at operator discretion. In such a manner, the system operator may simultaneously compare and analyze multi-dimensional segmental or entire region of interest views taken over distinct time periods. Such distinct time periods may include, for example, before and after medical treatment of the region of interest.

The user may also direct the system of the present invention to perform a comparative analysis on respective data sets. The comparative analysis tool of the present invention allows parallel display of two or more image sequences obtained at distinct time periods, both quantitative and qualitative. Such a parallel display enables the user to compare the quantitative parameters of perfusion exactly in the same region of myocardium at different stages of a particular study (for example, before and after the PTCA or drug infusion). The comparative analysis tool also automatically calculates various values including multiple parameters of contrast opacification, values of the percentage of perfused area/not perfused area, and overlap between different myocardial areas. The comparative analysis tool is further programmed to selectively create relative data sets reflecting changes in segment or region of interest perfusion characteristics at distinct fine times. Such perfusion characteristics include, for example, contrast intensity changes over time based on echocontrast material flow through the region of interest.

The system of the present invention may be utilized in a variety of imaging applications. The system is suitable for analysis of all contrast ultrasound studies including cardiac, abdominal, obstetrics/gynecology. It may also be used for analyzing intravenous, intra-coronary, and intra-aortic injections of echocontrast material. In particular, the system of the present invention is able to provide quantitative analysis of images obtained through second harmonics imaging. Analysis results from this system may be deliverable to various forms of output such as magnetic storage disks or paper media.

The system of the present invention is contemplated to include three-dimensional representation of myocardial echocardiography, whereby the system is able to analyze and display analysis results for complete left ventricular myocardium. Such three-dimensional representation may also be used for analyzing images taken of various other organs. The present invention provides for optional automated subtraction between the images of maximal contrast enhancement and baseline data, before contrast injection occurs. In addition, a complete sequence of images from the baseline to a complete contrast washout point may be analyzed by the present system.

The system of the present invention also preferably includes the capability of automatically dividing all myocardium (or other organs) into segments or regions of interest, as defined by the user. Thus, the user may set the number of segments to be used and subsequently analyzed. Furthermore, the system of the present invention may automatically calculate and display pixel intensity, segment number and other relevant parameters. Such analysis allows the system to obtain a complete contrast washin/washout data set for each segment and each myocardium (or any other organ) as a whole.

The comparative analysis tool of the present invention allows the system to compare a number of important parameters. For example, the system may compare size and location of perfusion defect area, both qualitatively and quantitatively. To effectuate such a comparison, the system displays the images side by side, and can compare images, for example, before and after a particular treatment. In addition, such side by side comparison enables detailed analysis of the same morphologically-well-defined structures, wherein the images may be defined as reference points for further calculations at subsequent time intervals.

The comparative analysis tool also allows the system to compare all contrast washin/washout parameters for exactly the same part of the respective myocardium (or other organs). By identifying particular locations in one image, the system of the present invention may automatically define and display the associated location on a distinct, but related image, and the compared images subsequently displayed side by side for simultaneous inspection. The comparative analysis tool also provides for complete time-intensity curve calculations by plotting the relationship between region ultrasonic echo intensity and time. Such intensity curves may then be displayed for investigating particular locations on two distinct, but related image sequences for the same organ, for example, before and after a particular treatment. Quantitative data may also be displayed for each image sequence as well as the quantitative comparisons between them.

A "crop" function may also be included in the present invention to identify a particular portion of respective images, and to subsequently utilize only that "crop" image data. Such a "cropping" function allows the system operator to focus on only particular data (particular portions of respective images) thereby saving space in the memory, saving user time in analyzing only pertinent data, and enabling the user to increase image resolution in particular areas of interest of the respective images.

A correction mode tool of the present invention enables the system to normalize (correct) values measured from the retrieved images. Such correction may be performed, for example, by dividing all of the values for each patient by the baseline in each respective region of interest or segment, or intensity values for other regions. Furthermore, such correction capability may utilize mean values of intensities in various regions, intensity values in particular locations in the respective images, or by fixed or floating value that is determined by the system operator.

In the analysis set up stage, the system user may view patient data, as well as specific imaging views which have been previously obtained. Such data directs the system to perform analysis in such a way so as to focus on particular image planes (views). In preferred embodiments, the number of images (frames) to be retrieved for subsequent calculation is preferably dictated by the system user.

In a preferred embodiment of the present invention, manual placing of desired regions are initially designated as rectangles for operator ease. However, the system preferably redefines such designated rectangles as ellipsoids to avoid artifacts from "corners" of the rectangles which may introduce irrelevant structures to the overall image. Furthermore, when the regions are chosen by the user, the system preferably allows the user to relocate such selected regions either individually or in combination to correct for image rotation or translation. In other embodiments, the system automatically relocates such regions to correct for any image rotation or translation.

The segmenting feature of the present invention may be performed automatically to account for the user-defined views. Data obtained with segmenting of two dimensional images may then be transformed/recalculated into a three-dimensional data set through the system of the present invention. The manual segmenting feature of the present invention provides for user-defined segmenting as without endo/epi (subendocardial/subepicardial parts of myocardium) division or with such division. Since most of the changes in myocardium occur first in the subendocardial layer, such an approach allows the user to increase the diagnostic capabilities of the system in detection of myocardial malperfusion.

The system of the present invention also allows the user to choose the calculation method utilized to generate respective data sets. In particular, the user may choose a desired medium value which allows for decreasing the influence of small image intensity heterogeneous fluctuations introduced in ultrasound imaging.

The analysis results are preferably stored and displayed as a three-dimensional data set, wherein each designated segment is preferably color coded. Relative color coding effectively shows the value of the parameter measured in each segment. In a particular embodiment, a sixteen segment model, standard to American Society of Echocardiography, has been used for division of the myocardium. The color coding approach provides a representation of complete left ventricular perfusion, and is of particular importance to the present invention. In other embodiments, images may also be displayed in gray scale, and two dimensional color coded segmented view of individual planes is also contemplated in the present invention.

In another embodiment of the present invention, the system may be used to image from inside the right hearts chamber, such as the right ventricle, so as to image entire cross-sections of the heart including the left ventricle. Such an embodiment allows the user to assess both morphology, function and perfusion with easy transvenous access. Perfusion imaging from inside the left ventricle may also be performed to obtain imaging using the system of the present invention.

A particular feature of the present invention provides a data analysis tool whereby imaging software 20 automatically filters unnecessary data from data sets being generated into various displays. Such a data analysis tool is operated through "local statistics", whereby mean intensity, median intensity, maximum intensity, and threshold intensity of ultrasonic reflectivity are automatically calculated for each data set. In addition, the data analysis tool automatically differentiates between baseline image fluctuations and accounts for the inherent variability of individual pixel intensity change in ultrasonic imaging. Thus, the system differentiates between essential and non-essential image changes over time to provide only that data necessary in analyzing perfusion characteristics in the region of interest. Such essential changes are developed by eliminating baseline data from the retrieved perfusion data sets, constituting a normalization procedure. Thus, temporary ultrasonic noise or background data previously obtained is automatically eliminated from analysis data sets prior to generation of the visual displays.

As a particular feature of the data analysis tool, imaging software 20 is preferably programmed to calculate individual pixel intensity change over predefined scanning time periods such that localized perfusion characteristics may be efficiently identified. Furthermore, the system is preferably programmed to calculate overall ultrasonic reflectivity intensity change throughout an entire segment, or throughout an entire region of interest for selected time periods. Such intensity changes over time may be plotted as time-intensity curves and subsequently simultaneously displayed and analyzed on display monitor 22.

As stated above, the system preferably calculates intensity within each segment or region of interest over a period of time, rather than a single data point. Therefore, a plurality of data points are preferably collated into distinct data sets representing predetermined periods of time for perfusion analysis. Such data sets may be preferably displayed by this system as time-intensity curves, whereby ultrasonic reflectivity intensity is plotted as a function of time in the selected segment or region of interest. To better reflect intensity change trends and overall perfusion characteristics, the system of the present invention is preferably programmed to implement a user-defined calculation method for obtaining a meaningful value for each intensity data point. For example, a plurality of data points taken from a single location may be displayed as a mean value of all such data points. In such a manner, the time-intensity curves generated for each segment or region of interest represent mean values throughout the time period being plotted. Such a calculation method produces the importance of noise and other background data on the overall data set, as well as increasing the diagnostic value of the calculated time-intensity curve. For further assistance in system operator analysis, the system of the present invention is preferably programmed to selectively simultaneously display such time-intensity curves, or other perfusion data sets from selected segments or regions of interest taken at distinct time periods, such as before and after medical treatment at the region of interest.

Preferably, the system of the present invention is programmed to obtain, generate, and analyze both segmented and non-segmented images of the particular region of interest, including the myocardium. Further, the system is preferably programmed to generate visually-perceivable displays including images and data sets representing both segmented and non-segmented images. To generate and calculate the local statistics for non-segmented images of the region of interest, a user-defined or automatically defined group of adjacent pixels/signals may be utilized in obtaining mean, media, etc. values for such data point. In a particular embodiment, the system of the present invention provides the user with an adjustable visual region indicating which group of adjacent pixels/signals are desired to be implemented in calculating the local statistics. Thus, normalization may be applied to the overall image as well as the segmented images.

An additional feature of the present invention includes the online or off-line capability to analyze the contractivity of particular regions of interest using ultrasonic contrast. In each pixel or electronic signal, the system analyzes intensity change over time, and calculates and generates a visually-perceivable map of the contractivity. A particular application of such contractivity analysis is an endocardial movement measurement to display the ventricular contractivity. An important aspect of this feature is that such contractivity studies may be performed with or without echocontrast material injection. Thus the cross-sectional area of the region of interest may be calculated at any moment in time.

In a particular embodiment, the diastolic phase of myocardium contraction is automatically divided by the system of the present invention into predefined segments of equal cross-sectional area. The thickness of each segment may then be calculated by the system and compared to respective segments to determine systolic thickening and other myocardial characteristics. In addition, derivatives of electronic signal intensity in contractivity studies may be calculated by the system to reflect amplitude, velocity, and acceleration of myocardial contraction.

The intra-vascular ultrasound catheter with microtechnology may be used in conjunction with intracardiac imaging. Such an ultrasound catheter is preferred over existing intra-vascular ultrasound transducers due to the fact that the block is increasing thickness in the direction parallel to the long access of the catheter.

The invention has been described herein in considerable detail in order to comply with the Patent Statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for obtaining and analyzing multi-dimensional in vivo images of blood perfusion through a targeted body region, comprising:
   a) providing computer-executable software operably configured to receive electronic signals via electronic communication means, said software being programmed to translate the electronic signals into electronic data, and to calculate and format the electronic data into visually-perceivable displays;
   b) providing an ultrasonic imaging device for generating the electronic signals representing corresponding ultrasonic image characteristics, said imaging device being operably coupled to said communication means for operably transmitting the electronic image signals therethrough;
   c) injecting an echocontrast material into a targeted body region;
   d) conducting a plurality of scans of said body region with said ultrasonic imaging device in one or more predefined time periods, said plurality of scans each obtaining reflection energy intensity data at a plurality of positions in the targeted body region, such that a plurality of reflection energy intensity data points are obtained for each of said plurality of positions;
   e) calculating a statistical median reflection energy intensity value among said plurality of reflection energy intensity data points for respective ones of said plurality of positions;
   f) generating an electronic image of said body region based on said median reflection energy intensity values; and
   g) displaying said electronic image of said body region on a viewable screen, said electronic image representing a multi-dimensional view of said body region, with said multi-dimensional view being automatically divided into a plurality of user-defined cross-sectional segment views graphically representing the entire body region for detailed analysis thereof.

2. A method as in claim 1 wherein said software is programmed to calculate individual body region position reflection energy intensity change over said time periods.

3. A method as in claim 1 wherein said software is programmed to calculate overall reflection energy intensity change over said time periods for each respective said segment.

4. A method as in claim 1 wherein said software is programmed to display a plurality of selected said multi-dimensional views obtained at distinct predetermined time periods.

5. A method as in claim 4 wherein said software is programmed to calculate and display a relative data set reflecting changes in multi-dimensional view characteristics between said distinct predetermined time periods.

6. A method as in claim 5 wherein said distinct time periods include before and after medical treatment.

7. A method as in claim 1 wherein said software is programmed to automatically determine size and location of a perfusion defect area, and to automatically compare data from respective corresponding perfusion defect areas.

8. A method as in claim 1 wherein said automatic segmentation of a myocardial region optionally includes sub-endocardial/subepicardial division.

9. A method as in claim 1 wherein said calculated electronic data is obtained throughout respective said predefined time periods, and is displayed as one or more time-intensity curves.

10. A method as in claim 9 wherein said software is programmed to selectively simultaneously display a plurality of time-intensity curves from one or more user-defined segments imaged in one or more said time periods.

11. A method as in claim 1 wherein said user-defined segments are compared to one another for respective reflection energy intensities at given scan times, with said segments being automatically relatively color-coded to illustrate relative perfusion characteristics among said plurality of segments.

12. A method as in claim 1 wherein said ultrasonic imaging device is an ultrasonic transducer.

13. A method as in claim 1 wherein said imaging device is coupled to a catheter device.

14. A method as in claim 13 wherein said imaging device is positioned adjacent said body region within a respective body vasculature.

15. A method as in claim 1 wherein said body region is at least a portion of the myocardium.

* * * * *